US00PP36057P2

(12) United States Plant Patent
Lim

(10) Patent No.: US PP36,057 P2
(45) Date of Patent: Aug. 6, 2024

(54) MINIATURE SHRUB ROSE PLANT NAMED 'ALTTICTAC'

(50) Latin Name: *Rosa hybrida*
Varietal Denomination: ALTtictac

(71) Applicant: Altman Specialty Plants Inc, Vista, CA (US)

(72) Inventor: Peter Lim, Escondido, CA (US)

(73) Assignee: Altman Specialty Plants Inc, Vista, CA (US)

( * ) Notice: Subject to any disclaimer, the term of this patent is extended or adjusted under 35 U.S.C. 154(b) by 0 days.

(21) Appl. No.: 18/371,518

(22) Filed: Sep. 22, 2023

(51) Int. Cl.
*A01H 5/02* (2018.01)
*A01H 6/74* (2018.01)

(52) U.S. Cl.
USPC ..... Plt./102
CPC ..... *A01H 6/749* (2018.05)

(58) Field of Classification Search
USPC ..... Plt./102
CPC ..... A01H 6/749; A01H 5/02
See application file for complete search history.

*Primary Examiner* — Keith O. Robinson
(74) *Attorney, Agent, or Firm* — Cassandra Bright

(57) ABSTRACT

A new and distinct cultivar of miniature shrub Rose plant named 'ALTtictac' is disclosed, characterized by distinctive pink and white striped flowers, blooming continuously from spring to autumn. Plants are dwarf and compact, with dark, glossy foliage exhibiting good resistance to blackspot disease and powdery mildew. The new variety is normally produced as an outdoor garden or container plant.

1 Drawing Sheet

Latin name of the genus and species: *Rosa hybrida.*
Variety denomination: 'ALTtictac'.

BACKGROUND OF THE INVENTION

The new *Rosa* cultivar is a product of a planned breeding program conducted by the inventor, Peter Lim. The objective of the breeding program was to produce new garden rose varieties with striped petals, and glossy foliage. The cross resulting in this new variety was made June 28 of 2013.

The seed parent is an unnamed, unpatented miniature *Rosa* variety. The pollen parent is the unpatented *Rosa* 'Love and Peace'. The new variety was selected in June 2014 by the inventor in a group of seedlings resulting from the 2013 crossing, in a nursery in Vista, California.

Asexual reproduction of the new cultivar has been performed by vegetative cuttings. This was first performed at a research greenhouse in Vista, California in June 2014 and has shown that the unique features of this cultivar are stable and reproduced true to type in more than 5 successive generations.

SUMMARY OF THE INVENTION

The cultivar 'ALTtictac' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALTtictac'. These characteristics in combination distinguish 'ALTtictac' as a new and distinct *Rosa* cultivar:

1. Pink and white striped petals.
2. Earlier blooming.

3. Dark, glossy foliage resistant to blackspot and powdery mildew.
4. Continuous flowering.
5. Dwarf, compact size.
6. Plants can be grown on their own roots; grafting is not required.

PARENT COMPARISONS

Plants of the new cultivar 'ALTtictac' are similar to plants of the seed parent, in most horticultural characteristics, however, plants of the new cultivar 'ALTtictac' differ in the following:

1. Flower color of the new variety is pink and white striped, while flower color of the seed parent is orange.

Plants of the new cultivar 'ALTtictac' are similar to plants of the pollen parent in most horticultural characteristics, however, plants of the new cultivar 'ALTtictac' differs in the following;

1. Flower color of the new variety is pink and white striped, while flower color of the pollen parent is pink and red striped.

COMMERCIAL COMPARISONS

Plants of the new cultivar 'ALTtictac' can be compared to the commercial variety *Rosa* 'Stars 'n' Stripes', U.S. Plant Pat. No. 4,029. These varieties are similar in most horticultural characteristics, however 'ALTtictac' differs in the following:

1. Flower color of the new variety is pink and white striped, while flower color of this comparator is red and white striped.

Plants of the new cultivar 'ALTtictac' can also be compared to the commercial variety *Rosa* 'POULTY019', U.S.

Plant Pat. No. 26,051. These varieties are similar in most horticultural characteristics, however 'ALTTICTAC' differs in the following:

1. Flower color of the new variety is pink and white striped, while flower color of this comparator is red and white striped.

BRIEF DESCRIPTION OF THE PHOTOGRAPH

The accompanying photograph illustrates in full color a close up of an individual flower of 'ALTtictac'. The plant producing this flower is approximately 18 months old; the flower is approximately 5 days old from a colored bud stage and about 2 days from fully open. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'ALTtictac' plants grown outdoors, in Vista, California. The growing temperature ranged from approximately 10° C. to 38° C. during the day and from approximately 5° C. to 22° C. during the night. Measurements were taken in September. General light conditions were very bright, normal sunlight. Measurements and numerical values represent averages of typical plant types.

Botanical classification: *Rosa* 'ALTtictac'.

Market classification: Miniature shrub rose.

PROPAGATION

Time to initiate roots: About 15 days at approximately 20° C.

Time to produce a rooted cutting: About 35 days at approximately 20° C.

PLANT

Age of plant described: Approximately 1.5 years.

Growth habit: Compact.

Container size: 2-gallon.

Height: 40 cm.

Plant spread: 50 cm.

Rootstock: Own root.

Growth rate: Moderate.

Branching characteristics: Sympodial branching.

Length of primary lateral branches: Average range 10 to 18 cm.

Diameter of lateral branches: Approximately 4 mm to 5 mm.

Quantity of branches: 10 to 12 main branches. Dense lateral branches.

Internode length: Average range 1.8 cm to 3.0 cm.

Branches-young wood:

*Diameter*.—Approximately 4 mm.

*Texture*.—Glabrous. No thorns.

*Color*.—Near RHS Green 143C.

Branches-Old Wood:

*Diameter*.—Approximately 5 mm.

*Color*.—Near RHS Green 137B.

*Texture*.—Glabrous. Almost no thorns.

Thorns:

*Approximately density/quantity of thorns*.—Young growth: No thorns present. Mature growth: Sparse to none.

FOLIAGE

Leaf:

*Arrangement*.—Alternate and compound.

*Quantity*.—Average 12 to 20 per main branch.

*Internode*.—Average range 8 mm to 1.5 cm.

*Average length*.—6.5 cm to 7.2 cm.

*Average width*.—4.0 cm to 4.5 cm.

Rachis:

*Length*.—1.8 cm to 2.3 cm.

*Diameter*.—Approximately 2 mm.

*Color*.—Upper surface: Near RHS Green 137B. Lower surface: Near RHS Yellow-Green N144C.

*Texture*.—Glabrous, all surfaces.

Leaflet:

*Quantity*.—3 or 5 per leaf, most commonly 3.

*Length*.—Approximately 2.1 cm to 3.1 cm.

*Width*.—Approximately 1.4 cm.

*Shape of blade*.—Broad ovate.

*Apex*.—Acute.

*Base*.—Broadly rounded.

*Margin*.—Finely serrate.

*Appearance of top surface*.—Moderately glossy.

*Appearance of bottom surface*.—Matte.

*Texture of top surface*.—Glabrous.

*Texture of bottom surface*.—Glabrous.

*Color*.—Young foliage upper side: Near RHS Green 137A flushed 139A. Serrations along margin near Greyed-Purple 187A. Young foliage under side: Near RHS Green 138A. Serrations along margin near Greyed-Purple 187B. Mature foliage upper side: Near RHS Green 137A. Serrations along margin near Greyed-Purple 187A. Mature foliage under side: Near RHS Green 138A. Serrations along margin near Greyed-Purple 187B.

*Venation*.—Type: Reticulate. Venation color upper side: Near RHS Yellow-Green N144B. Venation color under side: Near RHS Yellow-Green 145A.

Petiole:

*Length*.—Approximately 1.8 cm to 2.2 cm.

*Diameter*.—Approximately 3 mm.

*Color*.—Upper surface: Near RHS Yellow-Green 144B. Lower surface: Near RHS Yellow-Green 144C.

*Petiole wing*.—Typically 10 mm to 12 mm long and 5 mm wide. Apex apiculate. Upper surface colored near RHS Green 137C, lower surface colored near Green 137D.

*Texture*.—Glabrous.

FLOWER

Natural flowering season: Spring until autumn.

Inflorescence type and habit: Average 6 single flowers arranged on terminal flower stems. Fully double rotate flowers.

Rate of flower opening: Approximately 9 days from bud to fully opened flower.

Flower longevity on plant: 8 to 14 days, after fully opened.

Quantity of flowers: 50 to 80 flowers and buds.

Flower size:
*Diameter*.—Approximately 5 cm.
*Height*.—Approximately 2.0 cm.
Flower shape:
*From above*.—Round to very slightly irregular round.
*Profile of upper part of flower*.—Flattened dome.
*Profile of lower part of flower*.—Nearly flat.
Peduncle:
*Length*.—3.8 cm to 4.2 cm.
*Diameter*.—3 mm.
*Color*.—Near RHS Green 143C.
*Texture*.—Glabrous.
Petals:
*Petal arrangement*.—Multiple rotate, overlapping whorls.
*Petal quantity*.—Average 50 to 60.
*Length*.—2.0 cm to 2.5 cm.
*Width*.—1.5 cm.
*Shape*.—Obovate to wide obovate.
*Margin*.—Entire. Slightly ruffled.
*Apex*.—Rounded, slightly rolled under.
*Base*.—Very broad attenuate.
*Texture*.—Glabrous, all surfaces.
*Color*.—When opening: Upper surface: Near RHS Red 50A with streaks near White 155D. White streaking covers about 10 to 20% of petal surface. Very small basal blotch near White 155D. Lower surface: Near RHS Red 53D with streaks near Red 50D. 50D streaking covers about 10 to 20% of petal surface. Very small basal blotch near White 155D. Fully opened: Upper surface: Near RHS Red 51A flushed Red-Purple 58B. Streaked near White 155D. White streaking covers about 10 to 30% of petal surface. Very small basal blotch near White 155D. Lower surface: Near RHS Red-Purple N57C with streaks near Red- Purple 62D. Streaking covers about 10 to 20% of petal surface. Very small basal blotch near White 155D. Aging: Upper surface: Near RHS Red-Purple 71D streaked White N155C. White streaking covers about 20 to 40% of petal surface. Very small basal blotch near White N155C. Lower surface: Near RHS Red-Purple 72D streaked White N155C. White streaking covers about 20 to 40% of petal surface. Very small basal blotch near White N155C.
Bud:
*Shape*.—Ovate.
*Length*.—Approximately 2 cm.
*Diameter*.—Approximately 1.8 cm.
*Color*.—Near RHS Red 50A marbled Red 53B and 53C. Streaks near Red 50D covering about 20%.
Sepals:
*Quantity*.—5.
*Length*.—1.0 to 1.5 cm.
*Width*.—5 mm.
*Shape*.—Deltoid.
*Apex*.—Apiculate. Weak sepal extensions.
*Margin*.—Entire.
*Texture*.—Pubescent upper surface, glabrous lower surface.
*Color*.—Interior Surface: Near RHS Green 138B. Exterior Surface: Near RHS Green 137C.
Receptacle:
*Height*.—5 mm.
*Width*.—7 mm.
*Shape*.—Domed.
*Color*.—Near RHS Green 138C.
Fragrance: Very faint to none. Very faint leafy, sweet smell, or no fragrance.

REPRODUCTIVE ORGANS

Stamens:
*Quantity*.—About 70.
*Filament length*.—Approximately 2 mm to 3 mm.
*Filament color*.—Near RHS White 155D.
Anthers:
*Length*.—2 mm.
*Shape*.—Narrow globular.
*Color*.—Near RHS Greyed-Orange 167A.
*Pollen*.—Color: Near RHS Greyed-Orange 167B. Quantity: Scant or none.
Pistil: Not observed.

OTHER CHARACTERISTICS

Seeds and fruits: Not observed.
Disease/pest resistance: Good overall disease resistance to normal pests and diseases typical of garden roses. Very good resistance to powdery mildew (*Podosphaera pannosa*) and blackspot diseases (*Diplocarpon rosae*).

What is claimed is:

1. A new and distinct cultivar of miniature shrub Rose plant named 'ALTtictac' as herein illustrated and described.

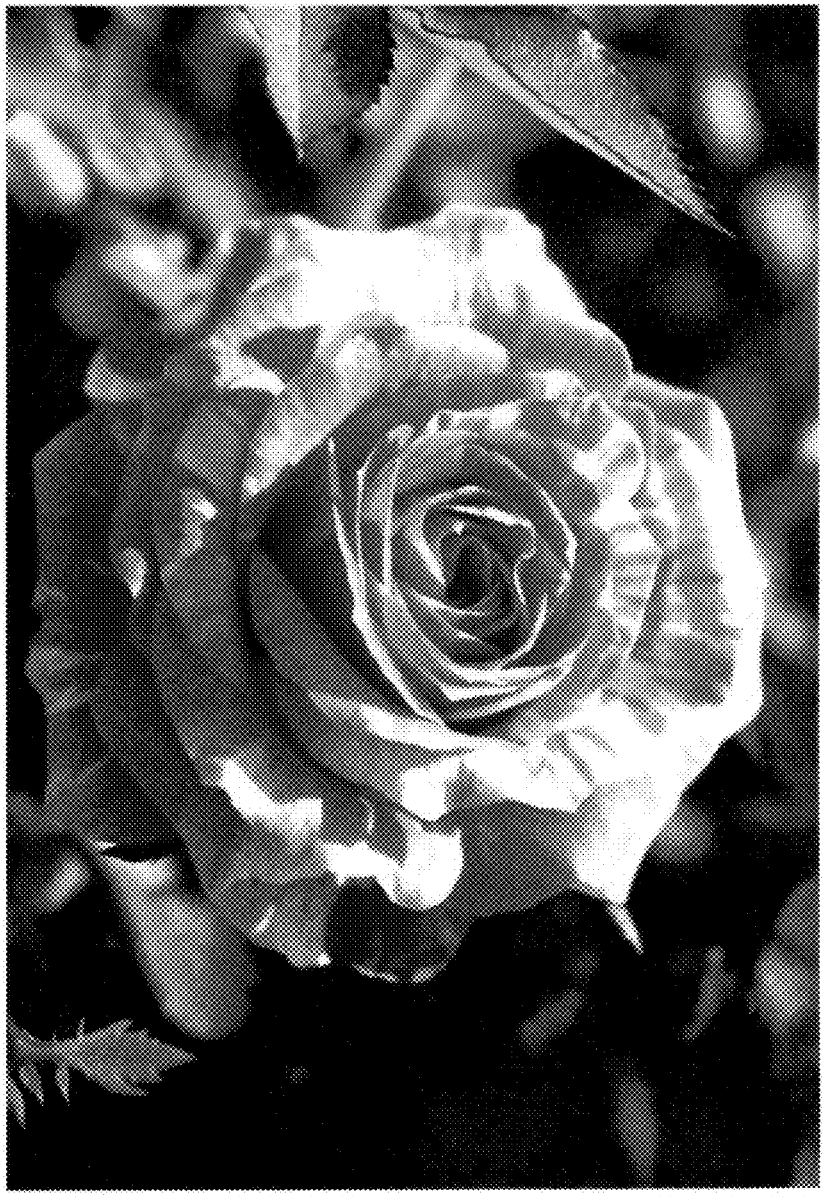

* * * * *